(12) United States Patent
Kaigala et al.

(10) Patent No.: US 11,117,131 B2
(45) Date of Patent: Sep. 14, 2021

(54) ELECTROKINETICALLY SEPARATING, ENCAPSULATING AND EXTRACTING ANALYTES ON A MICROFLUIDIC DEVICE

(71) Applicants: International Business Machines Corporation, Armonk, NY (US); Technion Research and Development Foundation Ltd., Haifa (IL)

(72) Inventors: Govind Kaigala, Rueschlikon (CH); Federico Paratore, Zurich (CH); Onur Gökçe, Zurich (CH); Moran Bercovici, Haifa (IL); Xander Van Kooten, Boskoop (NL)

(73) Assignees: INTERNATIONAL BUSINESS MACHINES CORPORATION, Armonk, NY (US); Technion Research and Development Foundation Ltd., Haifa (IL)

( * ) Notice: Subject to any disclaimer, the term of this patent is extended or adjusted under 35 U.S.C. 154(b) by 166 days.

(21) Appl. No.: 16/108,654

(22) Filed: Aug. 22, 2018

(65) Prior Publication Data
US 2020/0061616 A1 Feb. 27, 2020

(51) Int. Cl.
*B01L 3/00* (2006.01)
*G01N 27/447* (2006.01)
*C07K 1/28* (2006.01)

(52) U.S. Cl.
CPC ... *B01L 3/502746* (2013.01); *B01L 3/502715* (2013.01); *B01L 3/502761* (2013.01);
(Continued)

(58) Field of Classification Search
None
See application file for complete search history.

(56) References Cited

U.S. PATENT DOCUMENTS 8,304,253 B2 11/2012 Yi et al.
8,859,296 B2 10/2014 Schneider et al.
(Continued)

OTHER PUBLICATIONS

Borysiak et al. (Lab Chip, 15, 1697) (Year: 2015).*
Kaigala et al. (Angew. Chem. Int. Ed. 51, 11224-11240) (Year: 2012).*
Aebersold et al., "Mass spectrometry-based proteomics," Nature 422.6928, 2003, pp. 198-207.
(Continued)

*Primary Examiner* — J. Christopher Ball
(74) *Attorney, Agent, or Firm* — Cantor Colburn LLP; Daniel Morris

(57) ABSTRACT

Embodiments of the invention are directed to a method of separating and encapsulating an analyte on a microfluidic device in order to extract the analyte. A microfluidic device is provided having a main microchannel and a set of one or more auxiliary microchannels, each branching to the main microchannel at respective junctions therewith. A mixture is introduced as a single phase in the main microchannel in order to electrokinetically separate an analyte from the introduced mixture, and in order to confine the separated analyte in a microchannel portion of the main microchannel. The microchannel portion adjoins one of the junctions. One or more encapsulating volumes of an encapsulating phase are injected in the main microchannel via one or more of the auxiliary microchannels. The encapsulating phase is immiscible with said single phase. The encapsulated analyte is extracted from the main microchannel via one or more of the auxiliary microchannels.

12 Claims, 9 Drawing Sheets

(52) U.S. Cl.
CPC ......... *B01L 2200/0673* (2013.01); *B01L 2400/0421* (2013.01); *C07K 1/28* (2013.01); *G01N 27/44773* (2013.01)

(56) References Cited

U.S. PATENT DOCUMENTS

| | | | |
|---|---|---|---|
| 9,362,102 B2 | 6/2016 | Dovichi et al. | |
| 9,528,149 B2* | 12/2016 | Tsukuda | C12Q 1/686 |
| 9,683,961 B2 | 6/2017 | Breadmore et al. | |
| 2003/0170915 A1* | 9/2003 | Singh | G01N 33/58 436/518 |
| 2009/0217742 A1* | 9/2009 | Chiu | G01N 27/44717 73/61.55 |
| 2013/0105319 A1* | 5/2013 | Bhattacharya | B01F 13/0076 204/451 |
| 2016/0139078 A1* | 5/2016 | Henry | G01N 27/44765 204/645 |
| 2016/0327549 A1 | 11/2016 | Charlot et al. | |

OTHER PUBLICATIONS

Cheng et al., "Ripple structure-generated hybrid electrokinetics for on-chip mixing and separating of functionalized beads," Biomicrofluidics 8.6, 2014, 061102, 4 pages.

Ko et al., "Nanofluidic preconcentration device in a straight microchannel using ion concentration polarization," Lab on a Chip 12.21, 2012, pp. 4472-4482.

Li et al., "Integration of Isoelectric Focusing with Parallel Sodium Dodecyl Sulfate Gel Electrophoresis for Multidimensional Protein Separations in a Plastic Microfludic Network," Analytical Chemistry 76.3, 2004, pp. 742-748.

Li et al., "Sheathless electrokinetic particle separation in a bifurcating microchannel," Biomicrofluidics 10.5, 2016, 054104, 12 pages.

Lo et al., "Microchip DNA electrophoresis with automated whole-gel scanning detection," Lab on a Chip 8.12, 2008, pp. 2135-2145.

Paratore et al., "Isotachophoresis-Based Surface Immunoassay," Analytical Chemistry 89.14, 2017, pp. 7373-7381.

* cited by examiner

ELECTROKINETICALLY SEPARATING, ENCAPSULATING AND EXTRACTING ANALYTES ON A MICROFLUIDIC DEVICE

STATEMENT REGARDING FEDERALLY SPONSORED RESEARCH OR DEVELOPMENT

The work leading to this invention has received funding from the European Community's Seventh Framework Programme FP7/2007-2013 under grant agreement PITN-GA-2013-607322.

BACKGROUND

The invention relates in general to techniques for electrokinetically separating analytes and extracting separated analytes, in view of performing analyses or reactions involving the separated analytes. The invention further relates to microfluidic systems to implement such techniques.

Microfluidics deals with the precise control and manipulation of small volumes of fluids that are typically constrained to micrometer-length scale channels and to volumes typically in the sub-milliliter range. Prominent features of microfluidics originate from the peculiar behavior that liquids exhibit at the micrometer length scale. Flow of liquids in microfluidics is typically laminar. Volumes well below one nanoliter can be reached by fabricating structures with lateral dimensions in the micrometer range. Microfluidic devices generally refer to microfabricated devices, which are used for pumping, sampling, mixing, analyzing and dosing liquids.

Many microfluidic devices have user chip interfaces and closed flow paths. Closed flow paths facilitate the integration of functional elements (e.g., heaters, mixers, pumps, UV detector, valves, etc.) into one device while minimizing problems related to leaks and evaporation. The analysis of liquid samples often requires a series of steps (e.g., filtration, dissolution of reagents, heating, washing, reading of signal, etc.). Metallic electrodes are sometimes patterned in channels of the device. Microfluidic devices are used for various applications in life sciences.

In conventional separation techniques, chemical species are separated and collected at a macroscale, which implies relatively large volumes of liquids (i.e., milliliters), while samples are not confined (i.e., have low concentrations). On-chip separation methods have been proposed, which rely on microfluidics technologies and enable the separation and/or focusing of analytes at the microscale, thereby involving much smaller volumes of liquids, as noted above (i.e., ranging from nano- to pico-liters). Using electrokinetic separation methods, separated species are migrated along a sampling channel, in which detection can further be performed. Any detection or analysis need, however, be performed in the migration channel.

SUMMARY

Embodiments of the present invention provide a method of separating and encapsulating an analyte on a microfluidic device, in order to extract this analyte. The method relies on a microfluidic device having a main microchannel and a set of one or more auxiliary microchannels, each branching to the main microchannel at respective junctions therewith. A mixture is introduced as a single phase in the main microchannel, in order to electrokinetically separate an analyte from the introduced mixture, and so as to confine the separated analyte in a microchannel portion of the main microchannel. This microchannel portion adjoins one of the junctions. Next, one or more encapsulating volumes of an encapsulating phase are injected, in the main microchannel, via one or more of the auxiliary microchannels. The encapsulating phase is immiscible with said single phase. The injection is carried out so as to encapsulate the separated analyte in said microchannel portion. Finally, the encapsulated analyte is extracted from the main microchannel via one (or more) of the auxiliary microchannels.

The analyte can be separated by focusing said analyte in a given liquid band in said microchannel portion, using an isotachophoresis technique, whereby an electric potential is applied across the main microchannel. The focused analyte may for instance includes reaction products of species from the mixture as introduced in the main microchannel.

In embodiments of the invention, the extracted analytes are then brought to one or more extraction chambers of the device, which then allows various possible operations to be performed, which involve the extracted analyte(s), such as controlled dilution, detection (e.g., involving sensing surfaces), and/or chemical reactions.

Embodiments of the invention provide a method of separating, encapsulating and extracting an analyte such as described above, except that the microfluidic device now comprises an arrangement of auxiliary channels allowing two-dimensional separations. Namely, the device comprises a main microchannel, m secondary microchannels branching, each, from the main microchannel (m≥2), and m sets of ternary microchannels branching from respective ones of the secondary microchannels. That is, all ternary channels of a same one of the m set branch from a same one of the m secondary channels. Consistently with this design, a mixture can be introduced as a single phase in the main microchannel, in order to electrokinetically separate an analyte from the introduced mixture, and so as to confine fractions of the separated analyte in portions of the main microchannel. Next, the confined analyte fractions are transferred into the m secondary microchannels, for them to remain confined in a single phase therein. Encapsulating volumes and then injected, into each of the m secondary microchannels, via ternary microchannels branching therefrom, so as to encapsulate analyte fractions transferred in the m secondary microchannels. Again, the encapsulating volumes come from an encapsulating phase that is immiscible with the single phase in which the analyte fractions are confined. Finally, the encapsulated analyte fractions are extracted from the m secondary microchannels via some of the ternary microchannels branching therefrom.

Embodiments of the invention provide a microfluidic apparatus, which can be used to implement methods such as evoked above. The apparatus comprises a microfluidic device as involved in the above methods. In other words, the device comprises a main microchannel and a set of one or more auxiliary microchannels, each branching to the main microchannel at respective junctions therewith. In addition, the apparatus includes electrokinetic control means and flow control means. The electrokinetic control means are configured so as to allow an analyte to be electrokinetically separated from a mixture introduced as a single phase in the main microchannel and further confined in a portion of the main microchannel, which portion adjoins one of said junctions. The flow control means are configured to inject one or more encapsulating volumes of an encapsulating phase (immiscible with said single phase) in the main microchannel, via one or more of the auxiliary microchannels, so as to encapsulate a separated analyte in said microchannel portion. The flow control means are further configured to extract an encapsulated analyte from the main microchannel via one of the auxiliary microchannels.

Devices, apparatuses and methods embodying the present invention will now be described, by way of non-limiting examples, and in reference to the accompanying drawings.

BRIEF DESCRIPTION OF THE DRAWINGS

The accompanying figures, where like reference numerals refer to identical or functionally similar elements throughout the separate views, and which together with the detailed description below are incorporated in and form part of the present specification, serve to further illustrate various embodiments and to explain various principles and advantages all in accordance with the present disclosure, in which:

FIGS. 3-8C depict (partial) top views or architectures of microfluidic devices, as used in and/or according to embodiments of the invention, in which:

FIG. 3 depicts a device with a main channel, to which four transverse auxiliary channels connect, and further depicts constrictions and other liquid pinning features about the junctions and microchannel portions;

FIG. 8C illustrates another subsequent stage of how an encapsulated analyte can be extracted and split through a splitting tree, in order to parallelize subsequent operations on the split analytes, as in embodiments of the invention.

Figure 1:
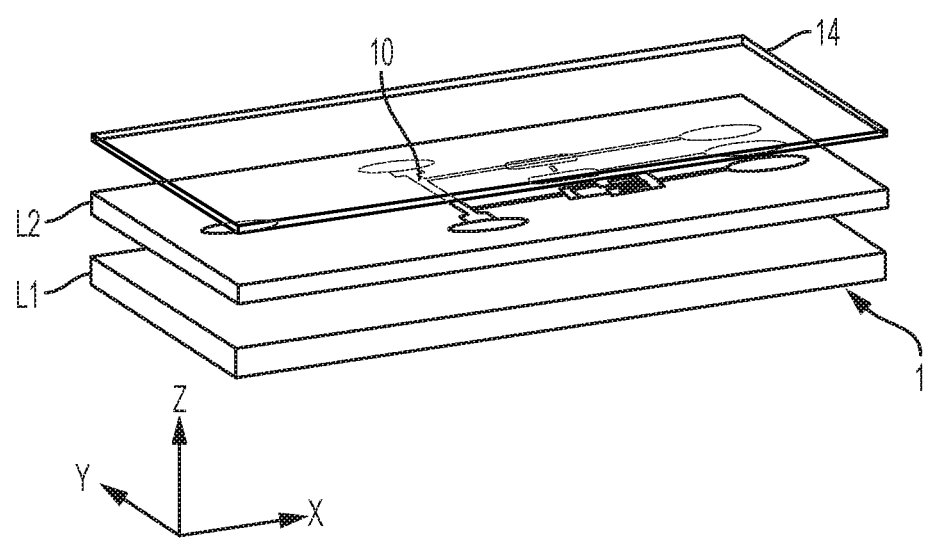
FIG. 1 is a 3D view of a microfluidic device, as involved in embodiments of the invention.

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION

As said in the background section, on-chip separation methods are known, which allows detection to be performed on the migration channel. Such methods, however, rely on device or systems that offer limited flexibility, inasmuch as the separated analytes cannot easily be stored or extracted, e.g., to be conveyed to detection or reaction chambers. Yet, it is desired to be able to retain the separated fractions of analytes, e.g., at high concentration and possibly for extended durations, ideally in a passive way (i.e., without applying an electric or magnetic field). Plus, many downstream analyses and reactions are not compatible with the electrokinetic separation and/or focusing performed in the migration channel. Starting from these observations, the present Inventors came to devise new methods and systems to collect the separated analytes directly on a microfluidic device ("on-chip") in a very practical way, as discussed in detail the following.

Referring generally to FIGS. 1-9, an aspect of the invention is first described, which concerns a method of separating and encapsulating an analyte on a microfluidic device, in view of extracting this analyte and, e.g., take additional steps, such as detection, dilution, reaction, etc.

This method requires S10 a microfluidic device 1-3, such as depicted in FIG. 1. This device comprises a liquid flow structure, which includes a main microchannel 10 (or sampling channel), as well as a set of auxiliary microchannels 11-13. Auxiliary microchannels 11-13 branch to the main microchannel 10 at respective junctions therewith. Note, this method may possibly be implemented on a device involving a single auxiliary channel 11 (in addition to the main channel 10). However, most embodiments of the invention described herein involve a plurality of auxiliary microchannels. Reasons for doing so will become apparent later.

Figure 2:
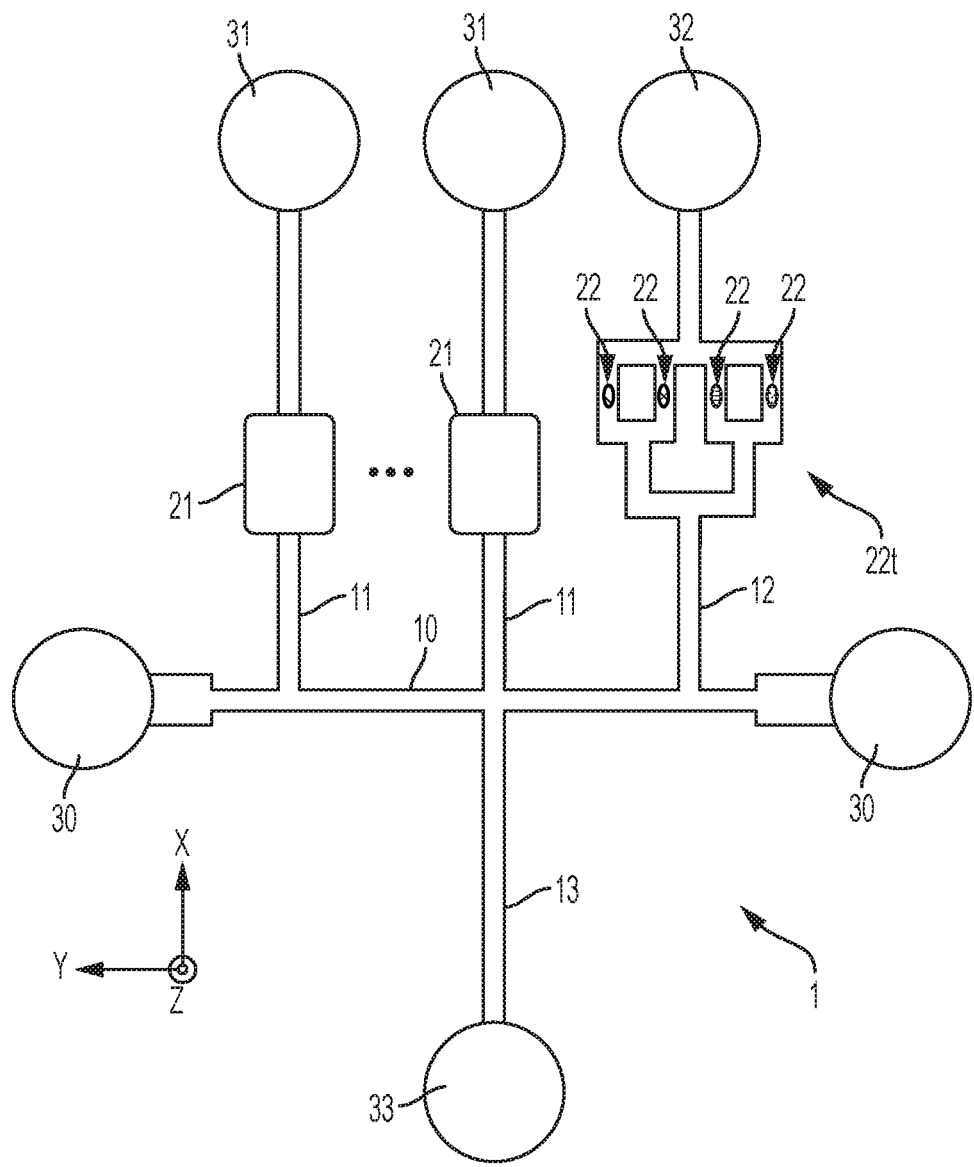
FIG. 2 is a diagram schematically illustrating how auxiliary channels of the microfluidic device interconnect with a main (sampling) channel thereof, as well as extraction chambers (e.g., used for detection and/or reaction purposes) connected to auxiliary channels, as involved in embodiments of the invention.

The devices 1-3 may otherwise comprise additional microfluidic structures (e.g., loading pads, detection, dilution or reaction chambers, capillary pumps, electrodes, etc.), which typically form part of or adjoin the flow path structure as depicted in FIG. 2. The liquid flow features (channels, chambers, valves and other pinning features, capillary pumps, loading pads, etc.) of the present flow path structures may possibly be patterned so as to have a same depth and, thus, be fabricated using a one mask/one-step process. In addition, such flow path structures are typically compatible with many materials, e.g., silicon, ceramics, polymers, this including dry film resists and classical photoresists.

The microchannels (also referred to as "channels") are typically formed as a groove patterned on a main surface of a layer L2 of the device (see FIG. 1). This layer L1 is for example a substrate, or any layer that is sufficiently thick to provide mechanical stability to the device 1, although mechanical stability may be provided by means of an additional, underlying layer L1, as assumed in FIG. 1. In all cases, the layer L2 may typically be an essentially planar object, such as a chip, a wafer or any such planar support. The layer L2 may possibly include various structures formed thereon or therein, in particular microstructures and other microfluidic features (not shown in the accompanying drawings), such as capillary pumps, loading pads, anti-wetting structures, flow resistors, vents, as well as electric circuits and contact pads. The flow path structure is typically covered (sealed) by a light-permissive layer L4, for detection/monitoring purposes.

A characteristic depth of the cavities formed by channels 10-15, chambers 21, 22 and other structures (e.g., vents, not shown) can be in the micrometer-length range, i.e., between 1 μm and 200 μm (and more specifically can be between 20 μm and 200 μm). Yet, some particular structures of the present devices 1-3 may be in the nanoscale range or in the millimeter range, the devices 1-3 as a whole typically being in the centimeter range. Widths (e.g., as measured in-plane) for the channels 10-13 will typically be in the micrometer-length range too (i.e., between 1 μm and 200 μm). Meanwhile, the average diameter of the chambers 21, 22 can be between 50 μm and 500 μm and, more specifically, can be between 100 μm and 200 μm. In the example of FIG. 1, the diameter of chambers 21, 22 is measured in-plane with the upper surface of layer L2, on which channels 10-13 are grooved), while a channel width is measured in-plane and perpendicularly to the direction of propagation of liquid in that channel. Normally, this width of the channels will be substantially smaller than the average diameters of the connected chambers.

Reverting to the present methods, a mixture 62 is introduced (step S20, FIG. 9) as a single phase in the main (sampling) channel 10 and an analyte 64 is electrokinetically separated (see FIGS. 5, 6) from the introduced mixture 62. This separation is carried out so as to confine the separated analyte 64 in a given channel portion 103, 104 (see also FIGS. 3, 4) of the main channel 10. Each junction (as formed by an auxiliary channel 10-13 with the main channel 10) adjoins a channel portion. In the examples of the accompanying drawings, each channel portion is delimited by two junctions, which delimit this portion.

Next, one or more encapsulating volumes 66 are injected S30 in the main channel 10, via one or more of the auxiliary channels 11-13, in order to encapsulate the separated analyte 64 in said channel portion 103, 104. Encapsulating volumes 66 come from an encapsulating phase 60 (e.g., oil, inert gas, as initially stored on the auxiliary channels), which is immiscible with said single phase (typically an aqueous phase). As a result of the encapsulation, each encapsulated analyte fraction is closed by two encapsulating segments. Note, two volumes 66 can be injected in the main channel 10, in order to separate the encapsulated fraction already in the main channel 10. However, only a single volume 66 may need be injected in the main channel 10, at a junction, as the other encapsulant part may stay in an auxiliary channel, from which the analyte fraction is then extracted, together with the previously injected volume 66.

In microfluidics, a droplet of liquid is usually defined as having a contact angle that is larger than 90 degrees (i.e., not wetting the surface or surfaces of the channel). Adopting this convention, the encapsulated analyte (which typically is in an aqueous phase) can be called a droplet, though it is typically referred to as a liquid segment, fraction, or volume. On the contrary, the encapsulating phase (e.g., oil) typically has a contact angle of less than 90 degrees. Thus, the encapsulating volumes 66 would typically not be regarded as droplets. Rather, such volumes 66 may be referred to as liquid plugs or segments.

The encapsulated analyte 65 is subsequently extracted S40 from the main channel 10, again via an auxiliary channel 11-13. Still, several encapsulated fractions of analytes may possibly be formed in the main channel 10, which may subsequently be extracted via any one or more of the (e.g., via respective) auxiliary channels 11-13. The present methods and apparatuses typically involve low-pressure systems to inject encapsulating volumes, and then extract and, if necessary, route the extracted analytes further down through the flow path structure (e.g., to storage, detection or reaction chambers).

The present approach allows for separation (and possibly focusing) of analytes, encapsulation and extraction thereof, directly on the microfluidic device, i.e., "on-chip". As the separated analytes are encapsulated, this, in turn, makes it possible to store and retain the separated fractions of analytes, possibly at high concentration and for extended durations. Once extracted, analytes can possibly be retained in a passive way (i.e., without applying and electric field, magnetic field, etc.) or brought to other locations, in order to perform additional operations. The extracted fractions of analytes may for instance easily be routed through auxiliary channels for subsequent analyzes and/or reactions, which may advantageously be performed on-chip, as in embodiments of the invention described below. In addition, the present approach does not require a solid (or otherwise non-flowing) phase. Still, it makes it possible to achieve a spatial confinement of analytes, in dedicated channel portions, thanks to the encapsulation.

Referring now to FIGS. 5, 6, the separation step can be carried out by focusing S20 the analyte in a given liquid band and in a respective channel portion 103, 104, using an isotachophoresis (ITP) technique, whereby an electric potential is applied S22 across the main channel. This results in a gradually increasing field across the channel 10. I.e., application of the electric potential yields a lower electrical field in the leading electrolyte (LE) and a higher electrical field in the trailing (or terminating) electrolyte (TE).

Figure 5A:
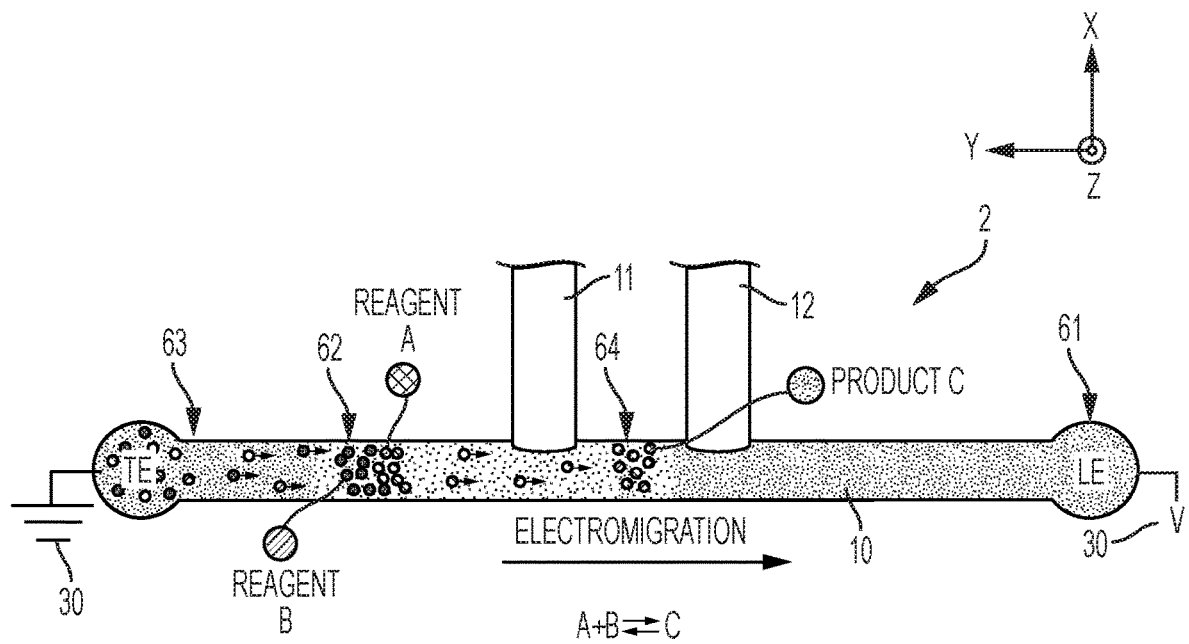
FIG. 5A illustrates how an analyte can be focused by isotachophoresis (FIG. 5A) prior to being encapsulated (shown in FIG. 5B) in accordance with embodiments of the invention, wherein the focused analyte includes reaction products C of species A, B from the mixture initially introduced in the main microchannel, and wherein a counterflow is applied in the main channel (shown in FIG. 5B) to compensate for the electromigration shown in FIG. 5A.
Figure 6A:
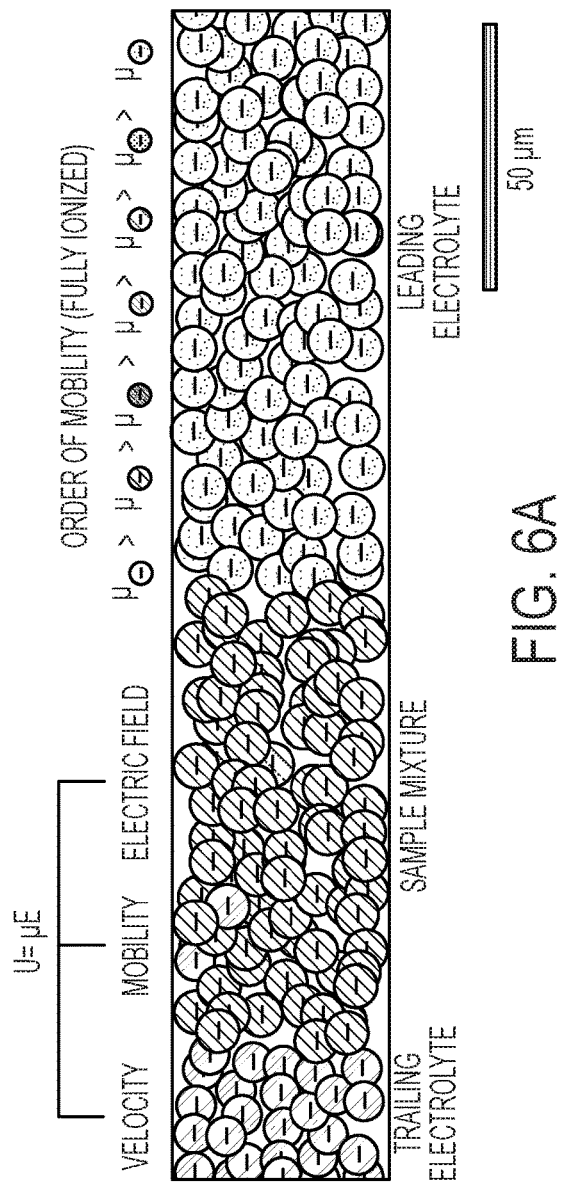
FIG. 6A illustrates how analyte fractions of distinct analytes can be separated from an initial mixture and focused by isotachophoresis in distinct liquid bands owing to their distinct electrophoretic mobilities in accordance with embodiments of the invention.

In detail, species of decreasing electrophoretic mobilities are successively injected in the main channel 10, as illustrated in FIG. 6A. Such species include, in order of decreasing mobilities: a leading electrolyte 61, species of said mixture 62 (injected as a single phase), and a trailing electrolyte 63. I.e., species of the trailing electrolyte have a lower average mobility than species of the mixture 62, which have themselves a lower average mobility than species of the leading electrolyte. Then, an electric potential is applied, in order to focus a given analyte in a given liquid band by electromigration (see FIG. 5A).

Figure 5B:
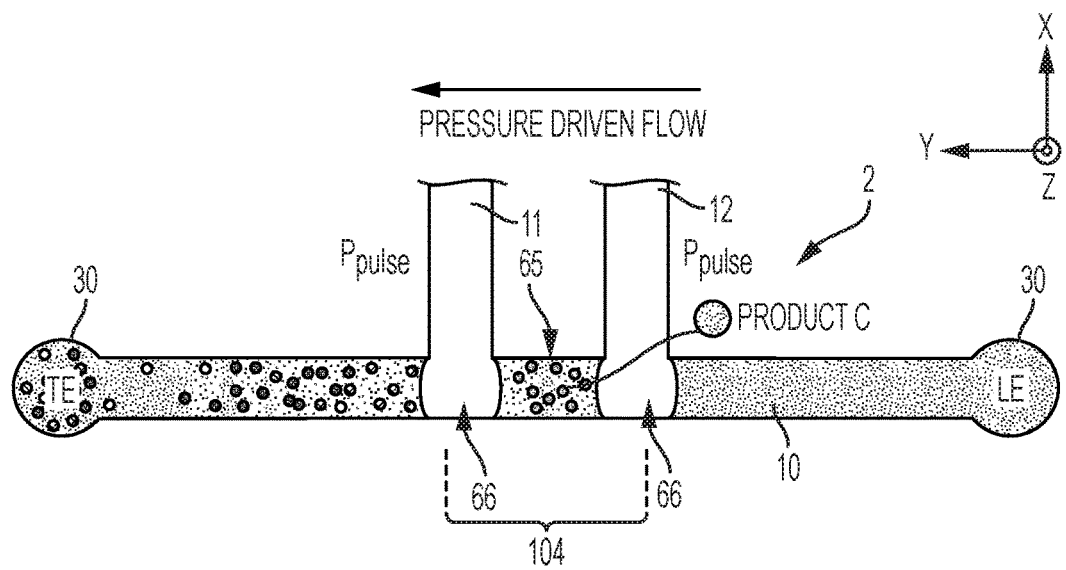
FIG. 5B illustrates how the analyte that was focused by isotachophoresis in FIG. 5A can be encapsulated in accordance with embodiments of the invention, wherein a counterflow is applied in the main channel to compensate for the electromigration shown in FIG. 5A.
Figure 6B:
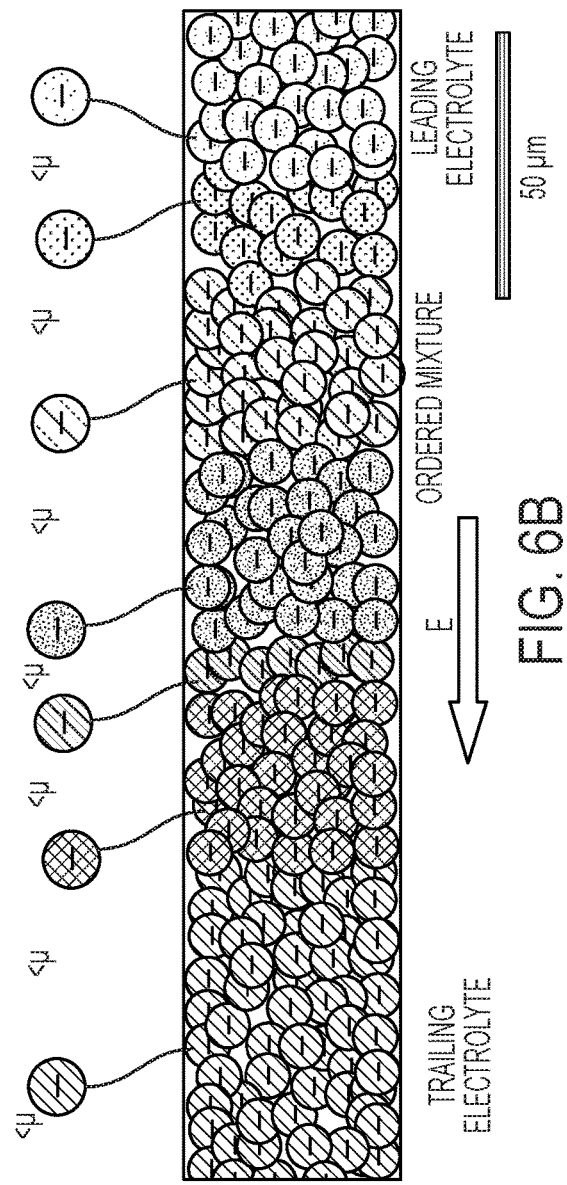
FIG. 6B illustrates the encapsulation of the analyte fractions of distinct analytes, which have been separated from an initial mixture and focused in distinct liquid bands in accordance with embodiments of the invention.

Eventually, one or more liquid bands of electrolyte get focused between the leading liquid band (mainly consisting of the leading electrolyte) and the trailing liquid band (the trailing electrolyte in the main channel), see FIG. 5A, 6B. Note, the focused analyte 64 may include species A, B and/or reaction products C of the mixture 62, depending on whether said species react or not. In the example of FIGS. 5A and 5B, the focused analyte 64 is assumed to essentially include reaction products C obtained according to the chemical reaction A+B⇌C. Note, however, that ITP can be used to focus analytes, irrespective of whether such analytes are meant to react or not.

In all cases, the migration is continued until a desired liquid band reaches a specific portion 103, 104 of the main channel 10, e.g., between two junctions formed by channels 11, 12 and, this, prior to encapsulating at least a part the desired liquid band, as depicted in FIG. 5B. This typically requires to apply a counterflow (e.g., pressure-driven) to compensate (at least partly) for the electromigration, as illustrated in FIG. 5B. Yet, a counterflow is not strictly required for ITP. If no counterflow is applied, the various liquid bands continuously move along the main channel 10, which, in turn, requires to precisely orchestrate the injection of encapsulants 66, to encapsulate the desired fractions.

Correspondingly, the present devices 1-3 shall typically form part of an apparatus (or system) that comprises control means 30 suited for applying a potential (to electrokinetically separate analytes) and a counterflow, e.g., pressure-driven, to compensate for the electromigration. That is, control means 30 shall typically include electrodes (coupled to an electrical circuit, part of which may reside on the microfluidic device 1-3, e.g., patterned thereon), a pressure-control system, as well as, e.g., computerized means, whereby the compensation can be adjusted to allow analyte fractions to be positioned in the channel 10. A pressure-driven flow directed oppositely to the electromigration direction allows a liquid sample to be anchored at a specific position along the main channel 10, and in particular, in a given channel portion 103, 104. This way, an analyte fraction can be confined in a respective channel portion 103, 104 of the main channel 10. As usual in the field, control means 30-35 shall typically include suitable monitoring and computerized devices.

In addition, this apparatus comprises flow control means 31, 33, 35 coupled to auxiliary channel(s) 11-15. Control means 31, 33, 35 are configured to inject encapsulating volumes 66 in an encapsulation channel 10, 14, via auxiliary channel(s) 11-13, 15, so as to encapsulate a separated analyte 64 in a given channel portion and later extract encapsulated analytes 65 via one or more auxiliary channels 11-13, 15.

As further illustrated in FIGS. 6A and 6B, several analyte fractions of distinct analytes may in fact be focused S20 (e.g., co-focused) in distinct liquid bands (again by ITP). The focused analyte fractions accordingly obtained can then possibly be confined in respective channel portions 103, 104, for subsequent encapsulation and extraction. The analyte fractions can for instance be extracted one at a time, from a same auxiliary channel or distinct auxiliary channels, which requires flow control.

ITP is compatible with any charged analytes, such as nucleic acids (e.g., DNA, RNA, mRNA, etc.), proteins, antibodies, bacteria, cells, particles, hormones, enzymes, small molecules (e.g. pesticides), and droplet emulsion. Using ITP, two or more analytes may be (co-)focused in respective bands, which can possibly be kept stationary by applying a counterflow to oppose the electromigration.

As evoked earlier, in the present context, an ITP system can be devised, which allows a chemical reaction to take place between analytes. In that case, the products of a chemical reaction will normally have a different mobility compared to the mobilities of the reagents, such that these products can be focused in different bands. Note, analyte fractions may be co-focused, i.e., focused directly side-by-side or, in described variants, be spatially separated, whereby some liquid separation is ensured between the two liquid bands containing the separated analyte fractions, in order to ease the encapsulation of the two liquid bands. Such a liquid separation is typically achieved by introducing a ionic spacer species at high concentration, having an intermediate mobility (comprised between the mobilities of the two analyte fractions of interest). This ionic spacer will thus focus between the two analyte fractions, in order to keep them separated, as known per se.

Still, as the one skilled in the art may appreciate, other electrokinetic methods can be contemplated in the present context, such as isoelectric focusing (IEF), ion concentration polarization (ICP), or capillary electrophoresis (CE) methods.

Figure 8A:
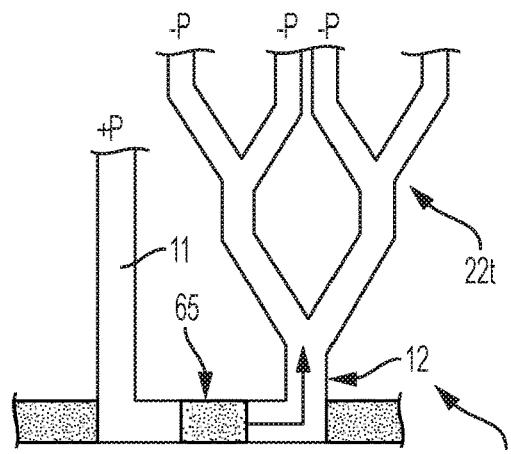
FIG. 8A illustrates an initial stage of how an encapsulated analyte can be extracted and split through a splitting tree, in order to parallelize subsequent operations on the split analytes, as in embodiments of the invention.
Figure 8B:
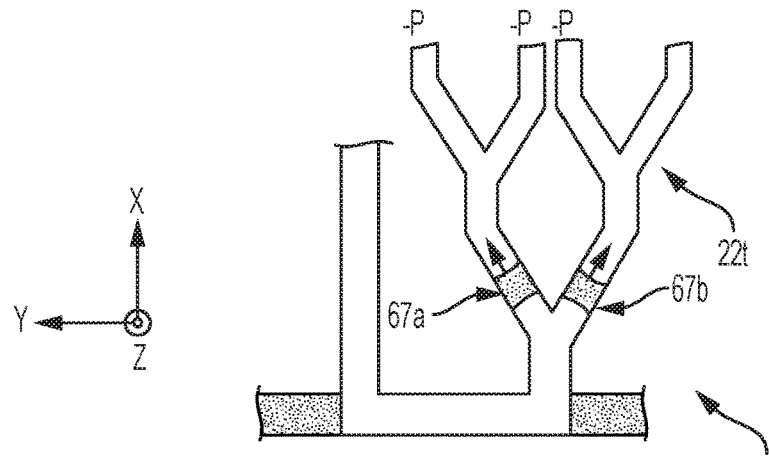
FIG. 8B illustrates a subsequent stage of how an encapsulated analyte can be extracted and split through a splitting tree, in order to parallelize subsequent operations on the split analytes, as in embodiments of the invention.
Figure 8C:
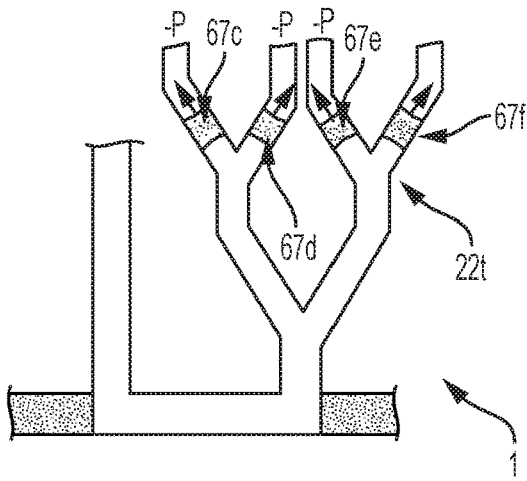
Figure 9:
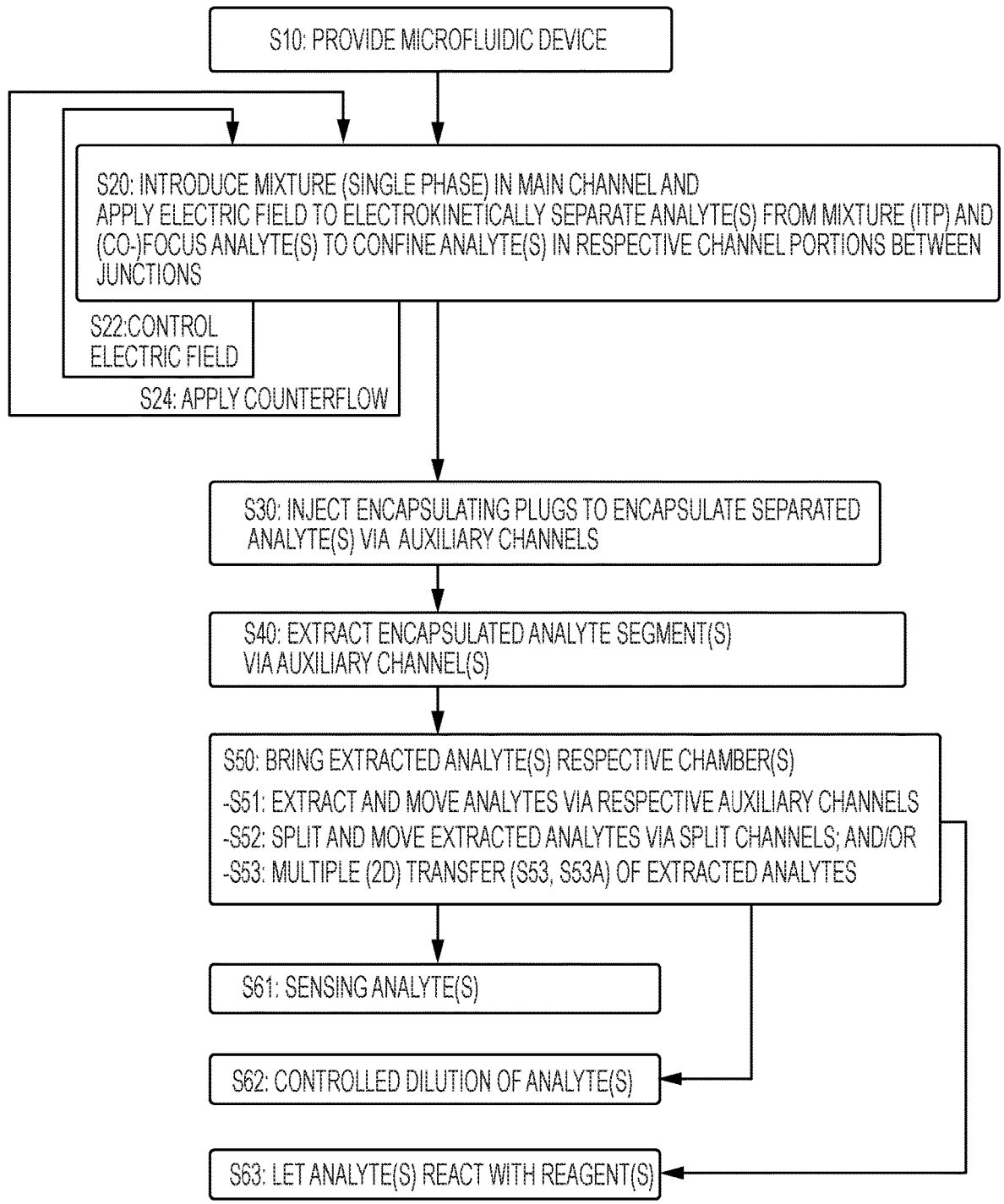
FIG. 9 is a flowchart summarizing high-level steps of a method of separating and encapsulating analytes, for extracting analytes and subsequently process such analytes, according to embodiments of the invention as otherwise illustrated in FIGS. 3-6B and 8A-8C.

As assumed in FIGS. 4, 5 and 8, the set of auxiliary channels 11-13 can comprises at least two auxiliary channels 11, 12, each joining the main channel 10 at a respective junction. The two corresponding junctions delimit a channel portion 104. Relying on two (or more) auxiliary channels eases the encapsulation and subsequent extraction. For example, a first encapsulating volume 66 may be injected S30 via the first auxiliary channel 11, while a second volume 66 is injected S30 via the second auxiliary channel 12, so as to encapsulate a separated analyte 64 as the latter is still confined in a channel portion 104, as illustrated in FIG. 5B. To that aim, two pressure pulses are applied (e.g., concomitantly) to the two channels 11, 12.

In variants, a single auxiliary channel may possibly be used to both insert encapsulants and extract the encapsulated species. At least one encapsulating volume 66 need be injected in the main channel 10 in that case, as aspiration from the auxiliary channel (that is already filled with the encapsulating phase 60) may suffice to close a confined liquid portion 64. That is, a single volume 66 may be injected in the channel 10, upstream from a given analyte fraction 64. Stop-and-go actuation of the liquid flow in the channel 10 will be helpful in that case. After injection, the partly encapsulated analyte fraction can be moved further along the channel 10, over a distance corresponding to its band extension length, and then anchored. Next, a depression applied to the single auxiliary channel (still filled with the encapsulating phase) causes to aspirate the analyte fraction, as well as the previously injected volume 66, back into the auxiliary channel. Yet, as one understands, using a single auxiliary channel requires precise flow control, be it to reverse the liquid flow in the main channel 10.

Thus, it is simpler to use at least two auxiliary channels 11-13 and inject two encapsulating volumes 66 in the main channel 10 to encapsulate a confined liquid portion, as exemplified in FIGS. 4, 5 and 8.

After encapsulation in the main channel 10, the encapsulated analyte 65 can be extracted S40 via one of the two auxiliary channels 11, 12 that were used to inject encapsulants 66. This is most simply achieved by applying a differential pressure between the two auxiliary channels, as further illustrated in FIGS. 4B and 8A (as denoted by symbols −P and +P).

More generally, n channel portions may be involved (n≥2) to confine analyte fractions in the main channel, by injecting encapsulants from n+1 auxiliary channels. In that respect, and referring back to FIGS. 2 and 3, the set of auxiliary channels 11-13 of the devices 1-3 may notably comprise a third auxiliary channel. The latter joins the main channel 10 at a third junction. Assume, in the example of FIG. 3, that the two leftmost channels 11 are used to inject encapsulating volumes 66 in the main channel, so as to encapsulate a fraction of liquid advancing along the channel 10. Then, after injection, the encapsulated analyte 65 may possibly be extracted S40 via the leftmost or middle channel 11 (assuming the analyte was adequately anchored in the channel portion delimited by the two leftmost channels 11). In variants, the liquid fraction may be extracted via the rightmost channel 12, in which case the liquid flow does not even need to be stopped in the main channel 10. In all cases, the analyte is typically extracted by applying a differential pressure between, on the one hand, the auxiliary channel from which it is to be extracted and, on the other hand, the remaining auxiliary channels.

Thus, multiple encapsulation and extraction scenarios can be envisioned, ranging from a single auxiliary channel (which requires accurate flow control) to n+1 auxiliary channels that define n channel portions.

After extraction, an analyte fraction 67 can for instance be routed to perform a variety of operations, e.g., involving controlled dilution, detection and/or reactions.

Figure 3:
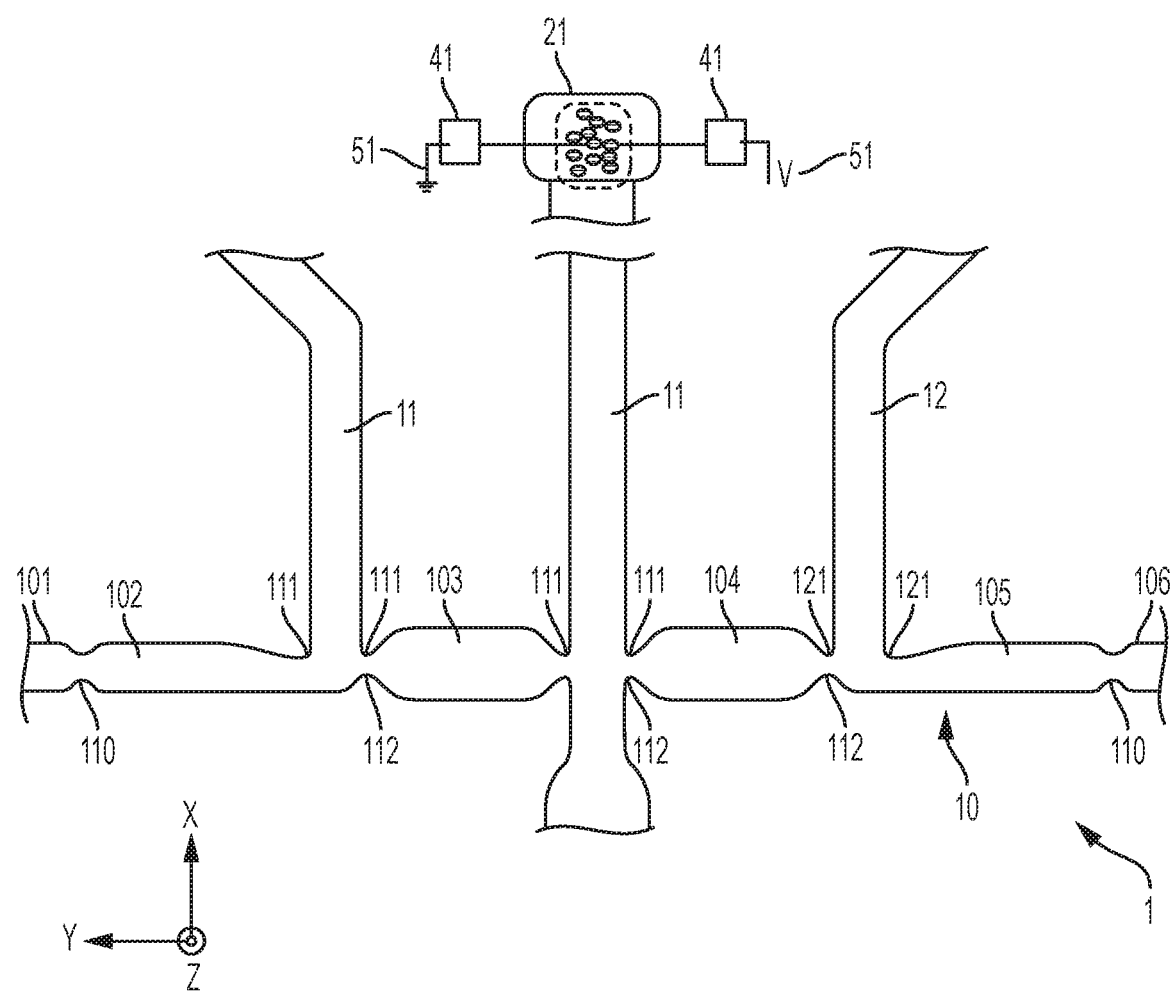

In that respect, and as shown in FIG. 3, the device 1 (or an apparatus or system that includes this device) may notably comprises a detection chamber 21. The latter is in fluidic communication with the auxiliary channel 11 through which the encapsulated analyte 65 is assumed to have been extracted in this example. In addition, sensing surfaces 41 are associated to (e.g., arranged in) the chamber 21, which components 41 are arranged at a certain minimal distance of the main channel 10, so as for the sensing performed via such components 41 to be essentially non-sensitive to the electric field resulting from the potential applied across the main channel, in operation of the device.

This way, the extracted analyte can be brought S50 to the detection chamber 21, for sensing 51, S51 the analyte via the sensing surfaces 41. Note, one or more sensing surfaces 41 may possibly be involved, depending on the actual detection techniques involved. Of particular interest is (surface-based) electrochemical detection. Electrochemical sensing (e.g., amperometric, potentiometric, etc.) can advantageously be used for glucose detection, protein analysis, nucleic acids and cells, amongst other examples. Electrochemical sensing relies on electrochemical reactions occurring at electrode surfaces 41 upon application of a potential drop. Electrochemical reactions are often limited by the concentration of the analyte and purity or composition of the sample. Electrokinetic focusing techniques are particularly suitable for increasing analytes concentration by several orders of magnitude. However, they rely on high electric fields, which are not compatible with electrodes 41 for electrochemical sensing.

More generally, beyond electrochemical sensing, detection based on nanowires, surface plasmon resonance (SPR) sensors and other sensors, which are sensitive to (or not compatible with) high electric fields may advantageously be contemplated in the present context.

As said, such detection techniques can advantageously be implemented on-chip. In variants, however, off-chip processes may be involved, e.g., using highly concentrated analytes mass spectrometry, sequencing, crystallography, etc.

Other applications may be devised. For example, referring to FIG. 2, the device 1 may further comprises a dilution chamber 21. Again, this chamber can be provided in the flow path structure of the device, i.e., on the device 1. In all cases, the dilution chamber 21 is in fluidic communication with the auxiliary channel 11 through which the encapsulated analyte 65 is extracted S40. There, the extracted analyte can be brought S50 to the dilution chamber 21 in order to perform S52 a controlled dilution of the analyte.

Other chambers may be dedicated to chemical reactions, which again can be implemented directly on-chip, and wherein reactions may possibly be performed in parallel. For instance, referring to FIGS. 2, 4 and 9, an extracted analyte 67 may possibly be brought S50 in a reaction chamber 22 (communicating with the channel 12 through which the encapsulated analyte 65 is extracted), so as for the analyte to react S53 with one or more reagents in the chamber 22. Note, a reaction chamber may possibly contain a dilution buffer to perform a controlled dilution prior to or after performing a reaction.

More generally, a variety of downstream analyses and/or reactions can be contemplated, be they on- or off-chip. For example, in the case of heterogeneous surface assays, certain reaction conditions may be met in a remote chamber 22, which would otherwise not be compatible with the electrokinetic system 10, 30 (e.g., due to high pH or high ionic strength). For homogeneous bulk assays, reactions can now be envisaged, which involve non-focusing reagents. Similarly, reagents that cannot be electrokinetically focused can be used in amplification reactions performed away from the channel 10 (but can be on-chip). Finally, as said earlier, downstream analyses can be devised on-chip, which involving surface-based sensing.

Referring now to FIGS. 2, 4 and 8, the devices 1-3 may further comprise a number of split channels 22t, where the channels 22t lead to respective chambers 22. The channels 22t define an arborescence, which can be regarded as a rooted tree extending from the main channel 10 to the chambers 22. Thus, liquid extracted from the channel 10 can potentially enter the chambers 22 via respective flow paths, gradually splitting from a common auxiliary channel 12, through which an encapsulated analyte 65 can be extracted S40. In other words, each of the split channels 22t splits from this channel 12 or from another one of the split channels.

The splitting tree allows the extracted analyte 65 to be successively split S52 through the channels 22t, whereby split fractions 67, 67a-f of analyte are obtained. As for example seen in FIGS. 4C, 4D, an analyte fraction extracted via the channel 12 (FIG. 4C) splits into two smaller fractions 67a, 67b at the secondary junction defined in the tree 22t. The splitting process may go on, as illustrated in FIG. 8, where secondary fractions 67a, 67b may subsequently split at ternary junctions (upper in the tree) to forms fractions 67c-f, and so on. This can again be achieved by applying suitable sets of differential pressures to the channels 22t (12) with respect to channel 11, as denoted by symbols –P and +P, and, if necessary, to the channel 10. This way, analyte fractions of gradually decreasing volumes may reach respective chambers 22, where they can in turn be analyzed, diluted, reacted, etc. Of particular advantage is the possibility to perform S51-S53 analyses and/or reactions (involving such split fractions) in parallel in the chambers 22, i.e., on-chip, as made possible thanks to the splitting tree 22t.

Figure 4A:
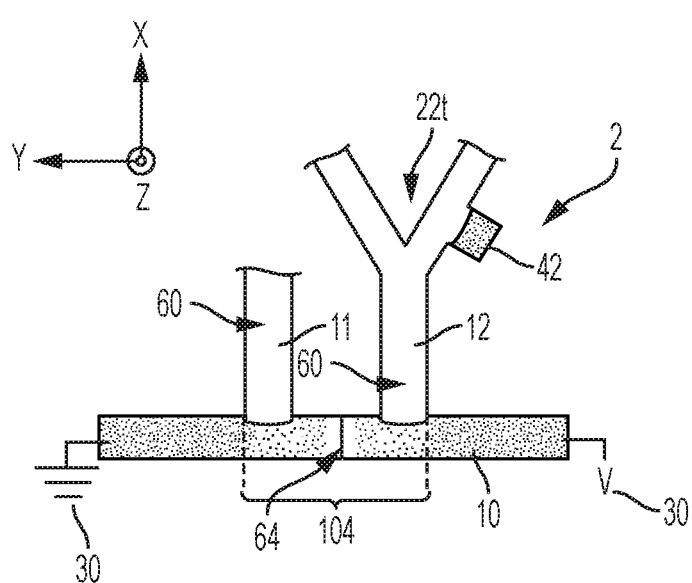
FIG. 4A illustrates various steps of a method according to embodiments of the invention, whereby an analyte is first focused in a channel portion between two junctions.
Figure 4B:
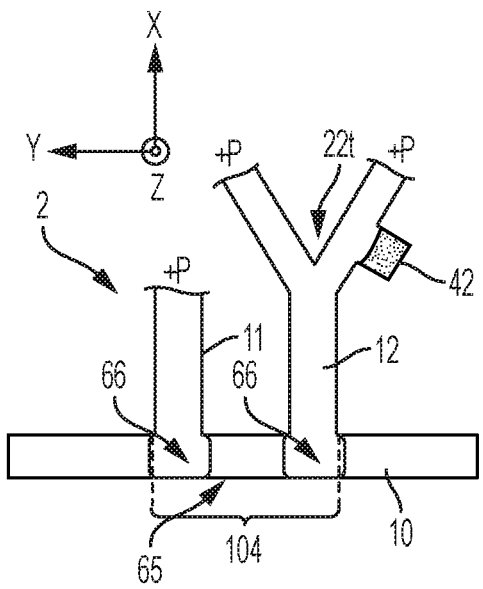
FIG. 4B illustrates various steps of a method according to embodiments of the invention, whereby the analyte that has been focused in the channel portion between two junctions is encapsulated.
Figure 4C:
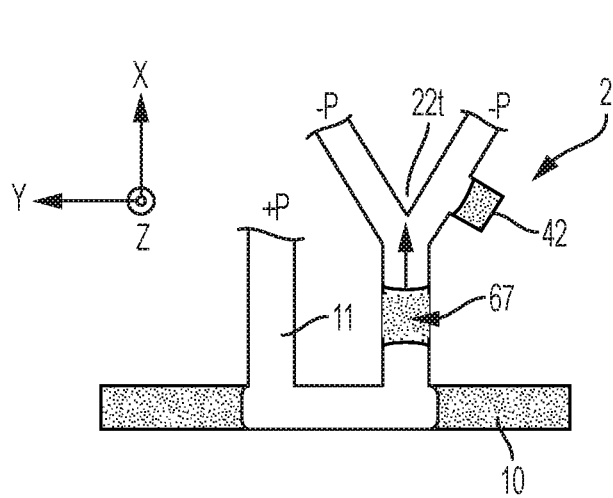
FIG. 4C illustrates various steps of a method according to embodiments of the invention, whereby the analyte that has been focused in the channel portion between two junctions and encapsulated is extracted.
Figure 4D:
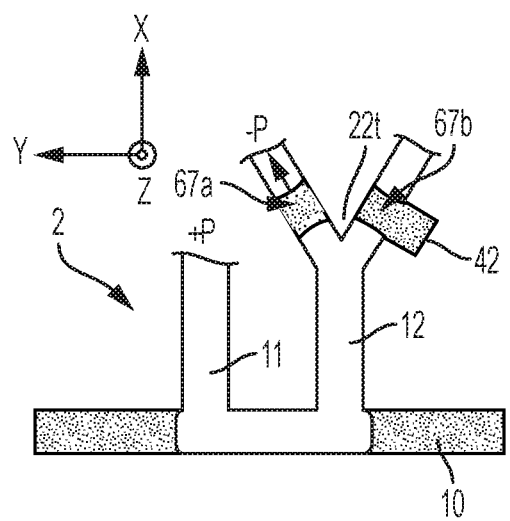
FIG. 4D illustrates various steps of a method according to embodiments of the invention, whereby the analyte that has been focused in the channel portion between two junctions, encapsulated, and extracted (FIG. 4C), is being split in view of further steps (e.g., dilution, reaction, detection, etc.)

Aspects of the methods and device features described above can advantageously be combined, in multiple ways. For example, FIG. 4A illustrates how focusing and/or separation of the analyte is carried out across a sampling channel 10 of a device 2. The electric field (e.g., a DC or AC field) is generated between electrodes 30 (e.g., external, patterned, etc.). The analyte is delivered to one or more encapsulation zones 104. As seen in FIG. 4B, the encapsulation of the analyte 64 can be achieved by injecting volumes of an immiscible phase 66 (e.g. oil, inert gas, etc.) through the auxiliary channels 11, 12, by, e.g., applying pressure, tuning the effective contact angle (e.g., using an electric field or surfactants), etc. Next, the extraction of the encapsulated analyte 65 is actively driven, e.g., using pressure control, FIG. 4C. Finally, downstream processes may notably include the delivery of the extracted analyte 67 to, e.g., a reaction chamber for it to react with reagents (for example for immunoassays, or transfection/transformation) and/or to detection chambers for sensing (e.g., electrochemical, optical). To that aim, the analyte 67 is split across a splitting tree 22t. Still, some of the resulting analyte segments 67a, b may possibly be extracted (from chambers communicating with terminal channels 22t) for off-chip analysis, if needed. As further seen in FIGS. 4A-D, a reaction chamber 42 (or reservoir) communicating with (e.g., inserted on the path of) a split channel may possibly be provided for reaction (in which case it comprises reagents) or dilution (it comprises a diluent) purposes, for example.

More sophisticated channel networks may further be contemplated, as illustrated in FIG. 7, which depicts a 2D arrangement of channels involving auxiliary channels 14 and secondary channels 15 branching from the latter 14. Such a channel network may advantageously be used to achieve a 2D separation of analytes, as explained below, in reference to another aspect of the invention.

According to this other aspect, the invention is embodied as a method of separation, encapsulation and extraction of an analyte, which is similar to the methods described in reference to FIGS. 2-6, and 8, 9, except that the microfluidic device 3 now comprises a more sophisticated flow path structure, which includes a main channel 10, as well as m secondary channels 14 branching, each, from the main channel 10, at respective, primary junctions. In the example of FIG. 7, m=3 secondary channels 14 vertically branch from the horizontal channel 10. More generally though, the flow path structure may include m≥2 secondary channels 14. Correspondingly, m sets of ternary channels 15 branch from respective secondary channels 14, at respective, secondary junctions. That is, all ternary channels 15 of a same set branch from a same secondary channel 14, as seen in FIG. 7, where the ternary channels 15 are horizontal in this example.

Figure 7A:
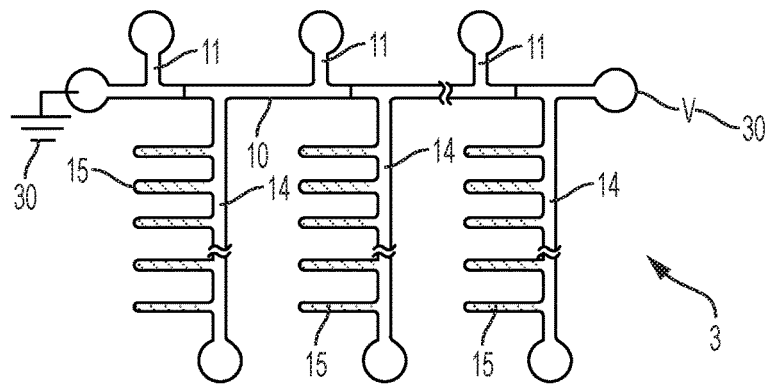
FIG. 7A shows another possible architecture of a device, which can be used to perform multi-dimensional extraction and separation of previously focused and encapsulated analytes, as involved in another aspect of the invention.

Consistently with the above architecture, a mixture can be introduced as a single phase in the main channel 10, in order to electrokinetically separate an analyte from the introduced mixture, as explained earlier. This way, fractions of the separated analyte can be confined in channel portions of the main channel 10, using electrokinetic control means 30, as depicted in FIG. 7A.

Figure 7B:
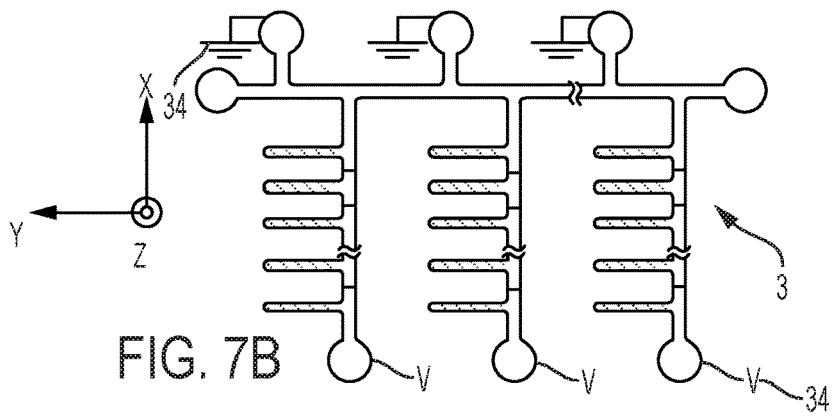
FIG. 7B shows another possible architecture of a device, which can be used to perform multi-dimensional extraction and separation of previously focused and encapsulated analytes, as involved in another aspect of the invention.
Figure 7C:
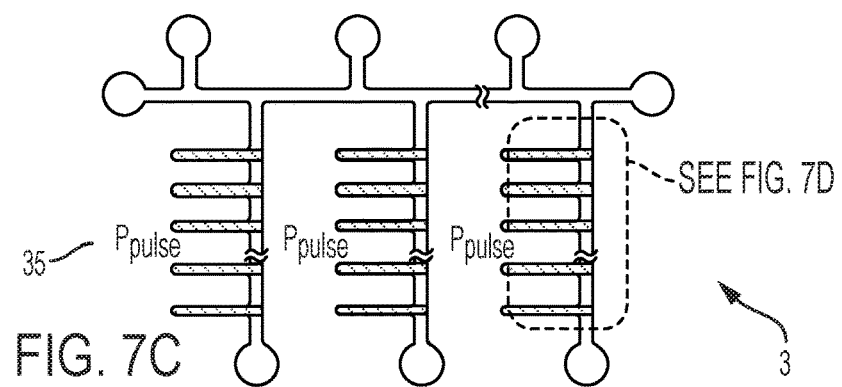
FIG. 7C shows another possible architecture of a device, which can be used to perform multi-dimensional extraction and separation of previously focused and encapsulated analytes, as involved in another aspect of the invention.
Figure 7D:
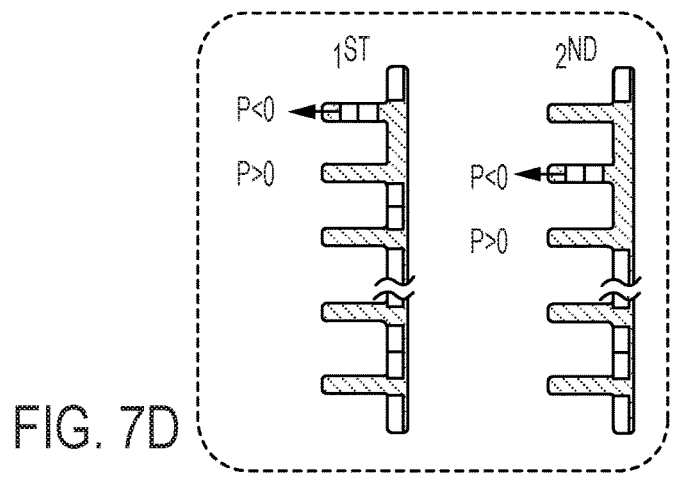
FIG. 7D shows another possible architecture of a device, which can be used to perform multi-dimensional extraction and separation of previously focused and encapsulated analytes, as involved in another aspect of the invention.

Next, the confined analyte fractions are transferred into the m secondary channels 14 (i.e., auxiliary channels). Because the fractions to be transferred are not encapsulated yet, the transfer into channels 14 is advantageously achieved by applying voltage biases (–V) to the channels 14, using voltage control means 34, as shown in FIG. 7B. This way, the analyte fractions remain confined in a single phase in the channels 14, even after the transfers into channels 14. In fact, and as it may be realized, a secondary separation can be performed upon transferring analyte fractions into the channels 14, by exploiting distinct electrical properties. For example, ITP may be used to perform the primary separation in channel 10 (based on electrophoretic mobility), while a secondary separation may be achieved by isoelectric focusing (IEF, based on isoelectric points), i.e., by applying suitable voltage biases, as shown in FIGS. 7A-B. In variants, mere pressure differentials may be applied to transfer the analyte fractions confined in channel 10.

In all cases, encapsulating volumes can then be injected into each of the m secondary channels 14, via ternary channels branching therefrom, so as to encapsulate the transferred analyte fractions in the channels 14. Again, this can be achieved by applying pressure pulses to the ternary channels 15. Encapsulating volumes again come from a phase (stored on the channels 15) that is immiscible with the phase in which the analyte fractions are separated and confined. Note, if a secondary separation is performed in channels 14 (e.g., by IEF), then the encapsulation of the further separated analytes need be performed after the secondary separation.

Finally, the encapsulated analyte fractions can be extracted from the m secondary channels via some of the ternary channels 15. I.e., in a given channel 14, encapsulated fractions are extracted via one or possibly more of the ternary channels 15 branching therefrom, following principles as explained earlier. Note, the transfer, encapsulation and extraction operations can all be performed concomitantly, first for each channel 14 and then for each channel 15.

As before, the channels 15 may possibly lead to chambers (not shown), whereby multiple analyses/reactions may be performed in output the channels 15, e.g., in parallel, on-chip.

A final aspect of the invention is now described, which concerns a microfluidic apparatus for separating, encapsulating and extracting an analyte. Most aspects of this apparatus have already been described earlier in reference to FIGS. 1-8 and the present methods of extraction. Thus, this apparatus is only briefly described in the following.

First, the apparatus comprises a microfluidic device 1-3, such as described above. I.e., the device 1-3 has a main channel 10 and one or more auxiliary channels 11-14, each branching to the main channel 10 at respective junctions therewith, see FIGS. 1-3.

In addition, the apparatus comprises electrokinetic control means 30, 34 and flow control means 31, 33, 35. Note, such means 30-35 may partly be formed on-chip. I.e., the device 1-3 may for instance comprises electrodes, electric circuit portions and tubing ports, to enable electrokinetic actuation, encapsulation and (e.g., pressure-driven) flow control. In addition, external monitoring (sensing, display) and controls (e.g., computers or panels suitably connected to electrical circuits and low-pressure systems) will typically be needed to achieve the needed electrokinetic/flow control 30-35.

The electrokinetic control means 30, 34 are configured so as to allow an analyte to be electrokinetically separated from a mixture 62, after the latter is introduced (as a single phase) in the main channel 10, in order for the separated analyte to get confined in a channel portion 103, 104 of the main channel 10.

On the other hand, the flow control means 31, 33, 35 are designed to inject encapsulating volumes 66 in the main channel 10, via the auxiliary channels 11-13, so as to encapsulate a separated analyte 64 in a channel portion 103, 104. The same flow control means are then used to extract encapsulated analytes 65 from channel 10 via one (or more) of the auxiliary channels 11-13.

As explained earlier in reference to FIGS. 4-6, the electrokinetic control means 30 may further be configured to focus a separated analyte 64 by isotachophoresis, so as for a focused analyte to get confined in a given liquid band in a channel portion 103, 104.

In particular, the microfluidic device 1-3 may further comprise one or more downstream chambers 21, 22 (i.e., chambers in fluidic communication with the auxiliary channels 11-13). It may notably include a detection chamber 21 communicating with one auxiliary channel 11 (FIG. 3), through which the encapsulated analyte 65 can be extracted, in operation. As said earlier, one or more sensing surfaces 41 may be associated to the detection chamber 21. E.g., they may form part of walls thereof. Still, such components 41 (and therefore the chamber 21) need be located sufficiently far from the main channel 10, so as to be essentially non-sensitive to the electric field resulting from the potential applied across the main channel 10, in operation.

As seen in FIGS. 2 and 3, the devices 1-3 may comprise any number of auxiliary channels 11-13. However, the device can comprise n+1 auxiliary channels (n≥2), which are distributed along the channel 10, such that the $k^{th}$ auxiliary channel branches to the main channel 10 at the $k^{th}$ junction. This defines n channel portions (such as portions 103, 104 in FIG. 3). That is, the $k^{th}$ channel portion extends between the $k^{th}$ junction and the $k+1^{th}$ junction (k=1, ... , n).

As explained earlier, most practical is to operate the electrokinetic control means in order to allow separated analytes 64 to be confined in respective channel portions, while the flow control means may be used to inject encapsulating volumes 66 in the main channel 10, via any pair of consecutive auxiliary channels, e.g., the $k^{th}$ and $k+1^{th}$ auxiliary channels, so as to be able to encapsulate a separated analyte 64 in any of the n channel portions. Applying differential pressures as shown in FIGS. 4, 8 then allows an encapsulated analyte 65 to be extracted from any of the n channel portions, via any adjoining auxiliary channel 11, 12.

Referring now more particularly to FIG. 3, the device 1 may advantageously comprise pinning features 111, 121 and, this, at each junction formed by adjoining channels 11-13 with the main channel 10. Such pinning features are adapted to pin the encapsulating phase 60 at the junctions. In the example of FIG. 3, the pinning features are formed as capillary stop valves, which form an opening angle (for encapsulating liquid coming from the channels 11-13) at the ingress of the channel 10. The opening angle is measured between a main longitudinal axis of a channel 11-13 (parallel to axis x in FIG. 3) about the valve and a lateral wall of the channel 10, to which channel 11-13 leads. By suitably devising the opening angle (together with the types of liquids involved and the [non-]wetting surfaces of channels), an encapsulating liquid flow coming from channel 11-13 shall normally be pinned at the ingress. A pressure pulse may nevertheless be applied, thus allowing the pinned liquid to overcome the pinning barriers.

In addition, each channel portions 103, 104 may comprises flow constrictions 111, 112, 121 at one or each end thereof. Such constrictions 111, 112 act as control points, which help in controlling the spread of the encapsulating phases and, in turn, in confining analytes in the channel portions 103, 104. Similarly, additional (outer) constrictions 110 may be formed along the main channel 10 between additional channel portions 101, 102, 105, and 106. All such constrictions may again be formed as more or less strong capillary valves, as assumed in the example of FIG. 3.

Finally, note that the inner pinning features 111, 121 may actually form part of the constrictions 111, 112, 121 that delimit channel portions 103, 104. In variants, the junctions formed by the auxiliary channels 11, 12 may be fully separated from the constrictions formed by the features 111, 112, 121. However, and as one may realize, there is no strict need to physically separate such junctions from the desired constrictions. A design such as proposed in FIG. 3 (whereby features 111, 121 formed at the junctions form part of the constrictions 111, 112, 121) actually eases the channel pattern processing and allows smaller encapsulated analyte volumes to be achieved in practice.

As further explained earlier in reference to FIGS. 2, 8, the microfluidic device 1-3 may further comprise a number of chambers 22 and a corresponding number of split channels 22t. Channels 22t form an arborescence, whereby each split channel splits either from a given one 12 of the auxiliary channels 11-13 or from another (parent) split channel 22t. Eventually, terminal channels typically lead to respective chambers 22, which may possibly communicate with other channels downstream, as assumed in FIG. 2.

The above variants can possibly be combined in multiple ways. For example, the device 1 shown in FIG. 2 depicts a general architecture of flow path structure, which can advantageously be used to perform methods as described earlier in reference to FIGS. 2-6 and 8. This architecture allows on-demand encapsulation with minimal dilution of electrokinetically separated and focused analytes in a two-phase fluid system.

The device 1 shown in FIG. 2 basically involves five modules. First, the sampling channel 10 (and corresponding control means 30) allows analytes to be electrokinetically separated and focused in an aqueous phase. Second, auxiliary channels 11-13 can be used to inject an encapsulating phase. Third, encapsulation zones are defined by channel portions 103, 104 (see FIG. 3), having a fixed volume, where the analyte of interest can be confined, thanks to control means 30. Fourth, extraction chambers 21 communicate with channels 11, which allow the encapsulated analytes to be extracted and stored, where controlled dilution or reactions with other reagents may take place. Finally, a splitting tree 22t is arranged on top of an extraction channel 22, thanks to which extracted analytes can be split into several volumes, thus enabling multiplexed reactions. If desired, the encapsulated analytes may nevertheless be extracted for off-chip analysis. Due to the two-phase encapsulation mechanism relied on, the extracted volumes remain fixed and no dilution takes place after encapsulation.

In other embodiments of the invention such as depicted in FIG. 7, the microfluidic device 1-3 may include a more sophisticated liquid path structure, e.g., including a network of separation channels 14, 15, with secondary channels 14 that branch from channel 10 and are connected to ternary channels 15. In such cases, voltage control means 34 are provided to apply voltage biases to the secondary channels 14, while pressure control means 35 are used to apply pressure pulses to the ternary channels 15.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, other materials than those explicitly cited may be contemplated.

What is claimed is:

1. A method of separating and encapsulating an analyte on a microfluidic device for extracting the analyte, wherein the method comprises:
   providing a microfluidic device having a main microchannel and a set of auxiliary microchannels branching to the main microchannel at respective junctions therewith, the set of auxiliary microchannels comprising a first auxiliary microchannel and a second auxiliary microchannel leading to the main microchannel at a first junction and a second junction, respectively;
   introducing a mixture as a single phase in the main microchannel and electrokinetically separating an analyte from the introduced mixture, so as to confine the separated analyte in a microchannel portion of the main microchannel, the microchannel portion between the first junction and the second junction;
   injecting, in the main microchannel, a first encapsulating volume comprising an encapsulating phase via the first junction and a second encapsulating volume comprising the encapsulating phase via the second junction, the encapsulating phase being immiscible with said single phase, so as to encapsulate the separated analyte in said microchannel portion between the first junction and the second junction; and
   extracting the encapsulated analyte from the main microchannel via the second junction of the second auxiliary microchannel.

2. The method according to claim 1, wherein separating the analyte further comprises focusing said analyte, by isotachophoresis, in a given liquid band in said microchannel portion, by applying an electric potential across the main microchannel.

3. The method according to claim 2, wherein the focused analyte includes reaction products of species from the mixture as introduced in the main microchannel.

4. The method according to claim 2, wherein the device further comprises:
   a detection chamber in fluidic communication with the auxiliary microchannel through which the encapsulated analyte is extracted; and
   associated to the chamber, one or more sensing surfaces arranged at a distance of the main microchannel, so as to be essentially non-sensitive to the electric potential applied across the main microchannel;
   wherein the method further comprises:
   bringing the extracted analyte to the detection chamber, and
   sensing the analyte via the one or more sensing surfaces.

5. The method according to claim 2, wherein focusing said analyte further comprises applying a counterflow in the main microchannel to at least partly compensate for the electromigration.

6. The method according to claim 2, wherein focusing said analyte further comprises focusing two or more analyte fractions of distinct analytes in distinct liquid bands, by isotachophoresis, one of said distinct analytes corresponding to said focused analyte.

7. The method according to claim 1, wherein:
   said microchannel portion is located between the first and second junction; and
   injecting encapsulating volumes comprises injecting a first encapsulating volume via the first auxiliary microchannel and a second encapsulating volume via the second auxiliary microchannel, to encapsulate the separated analyte as the latter is still in said microchannel portion, prior to extracting the encapsulated analyte.

8. The method according to claim 7, wherein the set of auxiliary microchannels of the microfluidic device provided further comprises a third auxiliary microchannel leading to the main microchannel at a third junction, whereby the second junction is between the first junction and the third junction, and the analyte is extracted via the third auxiliary microchannel.

9. The method according to claim 1, wherein:
   the device further comprises a dilution chamber in fluidic communication with the auxiliary microchannel through which the encapsulated analyte is extracted; and
   the method further comprises:
   bringing the extracted analyte to the dilution chamber, and
   performing a controlled dilution of the analyte in the dilution chamber.

10. The method according to claim 1, wherein the method further comprises:
    bringing the extracted analyte in a reaction chamber, the latter in fluidic communication with the auxiliary microchannel through which the encapsulated analyte is extracted, and
    letting the extracted analyte react with one or more reagents in said reaction chamber.

11. The method according to claim 10, wherein:
    the device further comprises a number of split microchannels leading to respective chambers, wherein each of the split microchannels splits from the auxiliary microchannel through which the encapsulated analyte is extracted or from another one of the split microchannels; and
    the method further comprises:
    splitting the extracted analyte through the split microchannels to obtain split fractions of analyte, and
    performing analyses and/or reactions involving the split fractions in parallel in said respective chambers.

12. A method of separating and encapsulating an analyte on a microfluidic device for extracting the analyte, wherein the method comprises:

providing a microfluidic device having a main microchannel, m secondary microchannels branching, each, from the main microchannel, m ≥2, and m sets of ternary microchannels branching from respective ones of the secondary microchannels, whereby all ternary channels of a same one of the m set branch from a same one of the m secondary channels, the m secondary microchannels comprising a first secondary microchannel and a second secondary microchannel leading to the main microchannel at a first junction and a second junction, respectively;

introducing a mixture as a single phase in the main microchannel and electrokinetically separating an analyte from the introduced mixture, so as to confine fractions of the separated analyte in microchannel portions of the main microchannel;

transferring the confined analyte fractions into the m secondary microchannels, for them to remain confined in a single phase therein;

injecting a first encapsulating volume comprising an encapsulating phase into the first secondary microchannel and a second encapsulating volume comprising the encapsulating phase into the second secondary microchannel via ternary microchannels branching therefrom, the encapsulating phase immiscible with said single phase, so as to encapsulate the analyte fractions; and extracting encapsulated analytes from the m secondary microchannels via the ternary microchannels branching from the second secondary microchannel.

* * * * *